United States Patent [19]

Clack

[11] Patent Number: 4,496,906
[45] Date of Patent: Jan. 29, 1985

[54] LIQUID CONDUCTIVITY MONITOR

[75] Inventor: Robert A. Clack, Monona, Wis.

[73] Assignee: Clack Corporation, Windsor, Wis.

[21] Appl. No.: 315,737

[22] Filed: Oct. 28, 1981

[51] Int. Cl.³ ............................................. G01N 27/02
[52] U.S. Cl. .................................. 324/439; 324/133; 324/450
[58] Field of Search ............... 324/446, 449, 450, 439, 324/133, 448, 99 D, 435, 442; 307/362, 363

[56] References Cited

U.S. PATENT DOCUMENTS

| | | | |
|---|---|---|---|
| 2,150,015 | 3/1939 | Witham | 324/442 |
| 2,760,152 | 8/1956 | Katz et al. | 324/442 |
| 2,985,821 | 5/1961 | Del Chiocca | 324/450 |
| 3,430,130 | 2/1969 | Schneider | 324/442 |
| 3,582,767 | 6/1971 | Brum et al. | 324/442 |
| 3,806,803 | 4/1974 | Hall | 324/133 |
| 3,919,627 | 11/1975 | Allen | 324/448 |
| 3,992,662 | 11/1976 | Koepnick et al. | 324/442 |
| 4,035,719 | 7/1977 | Anderson | 324/443 |
| 4,055,797 | 10/1977 | Doeleman | 342/442 |
| 4,156,179 | 5/1979 | Stephen et al. | 324/442 |
| 4,160,946 | 7/1979 | Frigato | 324/442 |
| 4,357,576 | 11/1982 | Hickam et al. | 324/449 |

Primary Examiner—Stewart J. Levy
Assistant Examiner—Kevin D. O'Shea
Attorney, Agent, or Firm—Lockwood, Alex, Fitzgibbon & Cummings

[57] ABSTRACT

A liquid conductivity monitoring device includes an elongated cylindrical housing having parallel-spaced electrodes at one end for insertion into a liquid carrying conduit, and a transparent user-viewable lens at its other end. The electrodes are connected within the housing to a differential amplifier which provides a change in output signal level when the liquid conductivity exceeds a predetermined threshold level. A pair of oppositely-poled LED's of different colors connected between respective unidirectional current sources and the output of the differential amplifier and viewable through the lens indicate acceptable and unacceptable conductivity levels to the user.

12 Claims, 12 Drawing Figures

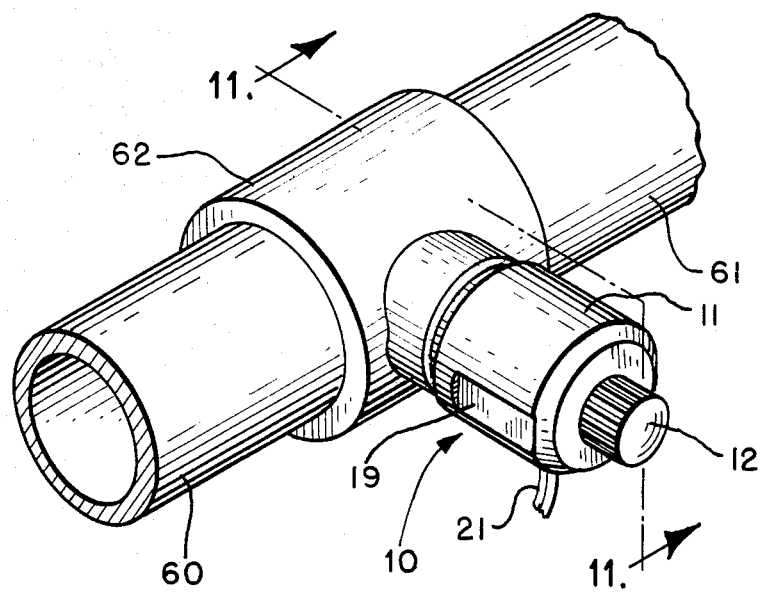
FIG.10
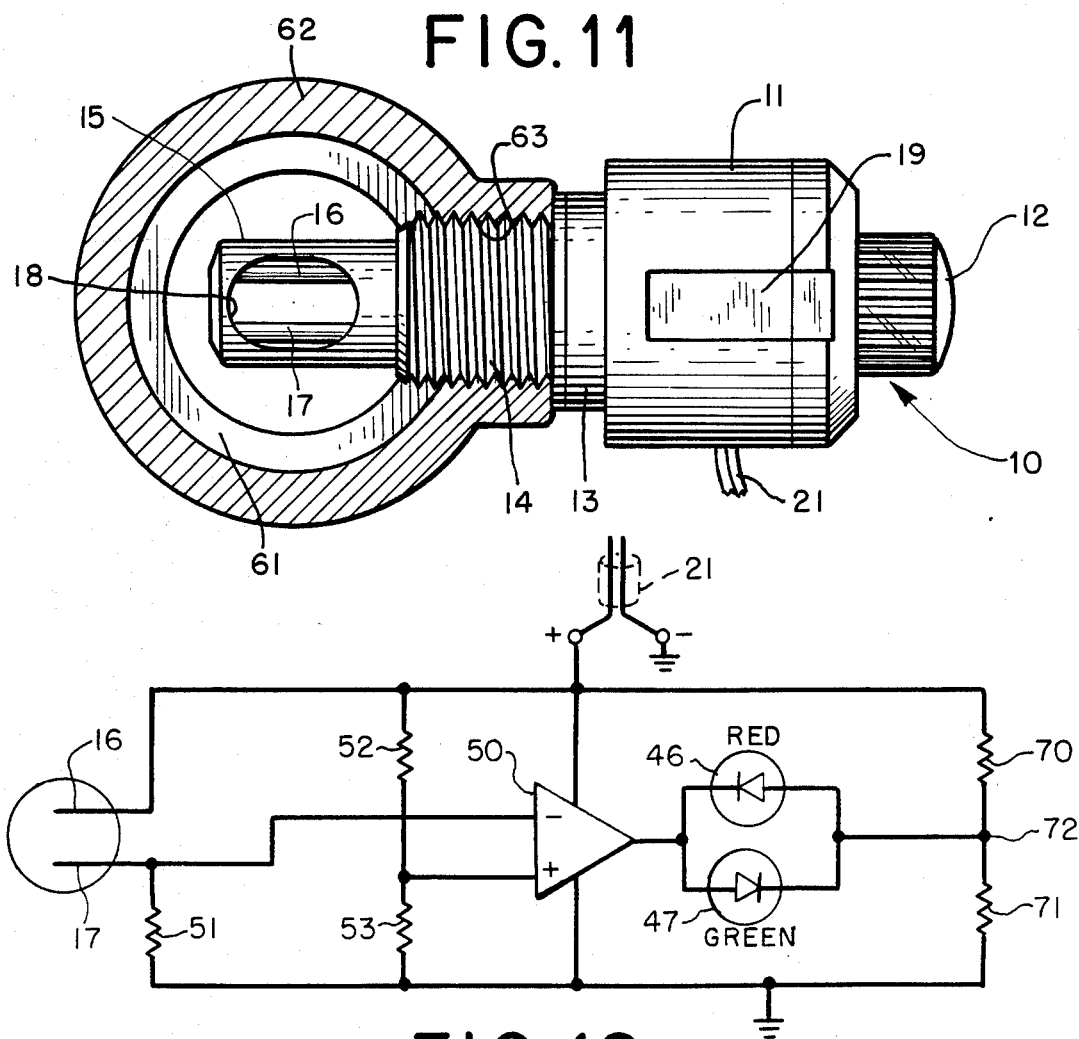
FIG.11
FIG.12

LIQUID CONDUCTIVITY MONITOR

BACKGROUND OF THE INVENTION

The present invention relates generally to liquid conductivity monitoring devices, and more particularly to devices which provide an output indication upon the conductivity of a monitored liquid exceeding a predetermined threshold level.

It is frequently necessary to monitor on a continuous basis the purity of water and other liquids. In the case of water, this is typically accomplished by monitoring electrical conductivity, since conductivity is proportional to the quantity of ionizable dissolved solids, which in turn is a function of the impurity content of the water.

Applications which require continuous real-time monitoring of water purity include monitoring the output of a deionization chamber, such as that used to purify water, and monitoring the water circulating through a boiler to prevent damage and encrustation of the boiler tubes by unpure water. Also, it is frequently necessary to monitor natural water sources, such as rivers, lakes, etc. for pollution.

In the laboratory, the measurement of water conductivity can be made with great accuracy and methods and apparatus for doing so have achieved a high degree of refinement. Unfortunately, the apparatus and methods utilized in the laboratory do not, as a practical matter, lend themselves to on-site monitoring wherein unambiguous pure (or acceptable) and unpure (or unacceptable) indications are required on a continuous basis, without any manipulation or calculation on the part of the observer.

One form of prior-art on-site water conductivity monitoring device provided a light output indication to indicate a sufficient level of purity. However, this device provided no light indication during an unpure or unacceptable condition, and thus in the absence of an indication an observer could not readily ascertain whether the water was unacceptable or the monitoring device was unpowered or inoperative. Accordingly, the need has existed for a water conductivity monitoring device which provides light output indications of both pure and unpure states, on a continuous and unambiguous basis. The monitoring device of the present invention provides such indications, and is compact and economical to construct, so as to readily lend itself to a wide variety of on-site monitoring applications.

Accordingly, it is a general object of the present invention to provide a new and improved liquid conductivity monitoring device.

It is a more specific object of the present invention to provide a liquid conductivity monitoring device which provides continuous unambiguous output indications of pure and unpure liquid states.

It is a further object of the present invention to provide a new and improved liquid conductivity monitoring device which is simple and compact in construction, and can be readily installed in-line in liquid flow systems.

SUMMARY OF THE INVENTION

The invention is directed to a monitoring device for monitoring electrical conductivity in a liquid. The device includes a pair of spaced-apart conductivity-sensing electrodes arranged for immersion in the liquid, and comparison amplifier means having at least one input terminal and an output terminal, the input terminal being coupled to the sensing electrodes, the output terminal changing from a first signal level to a second signal level upon the conduction between the electrodes exceeding a predetermined threshold level. The monitoring device further includes first and second sources of unidirectional current each having a signal level intermediate the first and second signal levels of the output terminal, and first and second light-emitting diodes connected between respective ones of the current sources and the output terminal, the diodes being oppositely poled from each other whereby the first light-emitting diode is forward biased to light only when the output terminal is at the first signal level to indicate conduction below the threshold level, and the second light-emitting diode is forward biased to light only when the output terminal is at the second signal level to indicate conduction above the threshold level.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 10 is a perspective view of the liquid conductivity monitoring device of the invention installed on an in-line connector.

FIG. 11 is a cross-sectional view of the monitoring device and in-line connector taken along line 11—11 of FIG. 10.

FIG. 12 is an electrical schematic diagram of an alternate circuit for the liquid conductivity monitoring device.

DESCRIPTION OF THE PREFERRED EMBODIMENT

Figure 1:
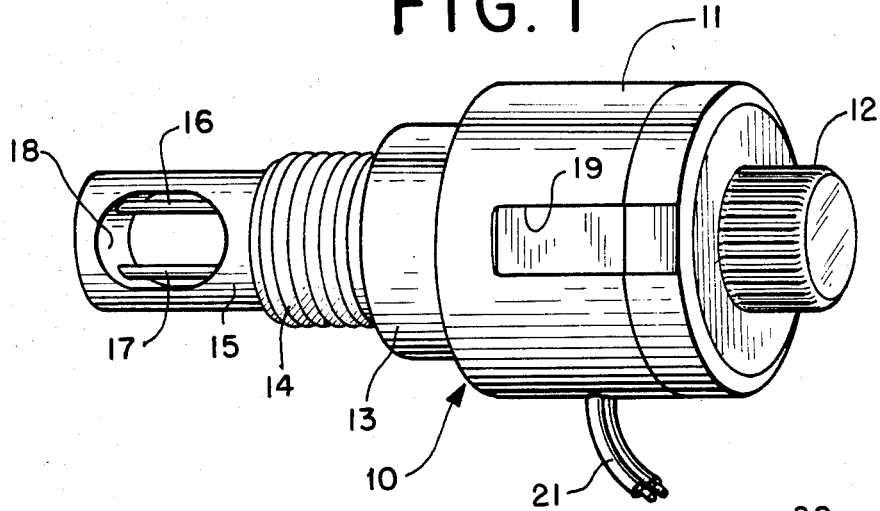
FIG. 1 is a perspective view of a liquid conductivity monitoring device constructed in accordance with the invention.

Referring to the Figures, and more particularly to FIG. 1, a liquid conductivity monitoring device 10 constructed in accordance with the invention is seen to comprise a generally cylindrical housing 11 formed of plastic or other electrically non-conductive material. A transparent lens cap 12 of generally cylindrical construction is attached to the front end of the housing. The rear end of the housing includes an unthreaded cylindrical body portion 13 and a threaded shank portion 14. Water conductivity is sensed by means of a probe portion 15 which extends from the end of the threaded mounting portion. A pair of conductivity-sensing electrodes 16 and 17 encapsulated in the probe portion 15 are exposed to liquid flow through an aperture 18.

In use monitoring device 10 is threaded or otherwise fitted into an aperture in the fluid conduit to be monitored, the threaded mounting portion 14 typically engaging complementary threads on the inside surface of the receiving recess. A pair of flat spots 19 may be provided on the exterior surface of housing 11 to facilitate engagement of the monitoring device with a wrench. Power for the monitor device is preferably provided by an external power pack 20 (FIG. 2) connected to the indicator by a flexible cable 21.

Figure 2:
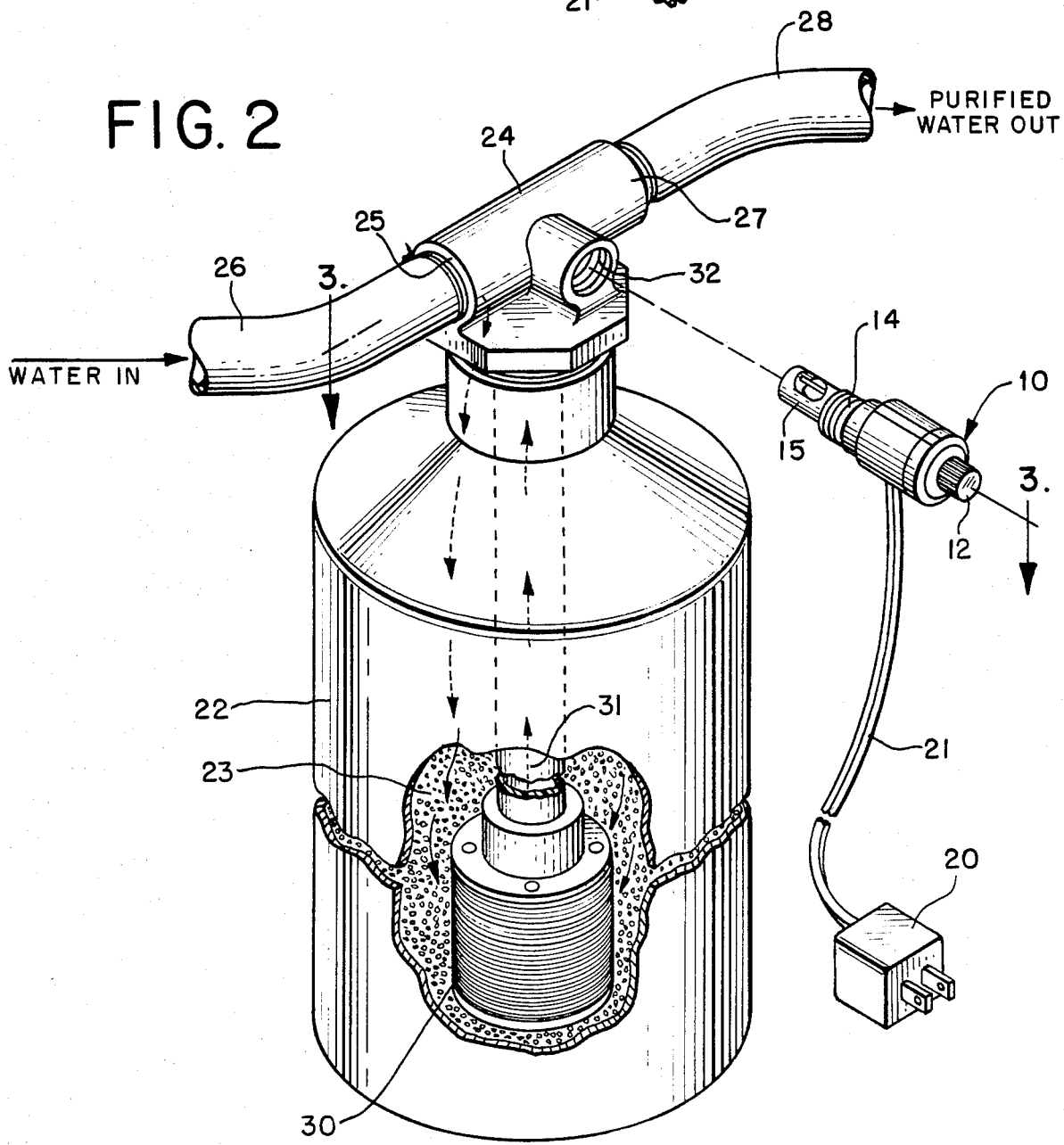
FIG. 2 is a perspective view of the liquid conductivity monitoring device of FIG. 1 installed on a water deionization chamber of typical construction.

One application wherein the liquid conductivity monitoring device of the invention is particularly attractive is in monitoring the output of a water deionization chamber, such as that shown in FIG. 2. This chamber, which can be conventional in construction and operation, includes a generally cylindrical upstanding tank 22 within which a plurality of plastic beads 23 of ion exchange resin are contained. Water is admitted and removed from the tank through an adapter head assembly 24, which may be similar to that presently marketed by the assignee of the present application as the Clack Model 890 adapter head assembly. This head assembly includes an inlet port 25 for connection to an inlet conduit 26, and an outlet port 27 for connection to an outlet conduit 28.

In operation, water received by head assembly 24 is discharged into tank 22 through an annular passageway at the rim of the head assembly. Deionized water having been exposed to the ion exchange resin beads 23 within the tank is collected by means of a screened intake basket 30 and returned to the adapter head assembly through a vertical conduit 31. The screened basket in accordance with conventional practice includes a plurality of flat annular filter discs which prevent individual ion exchange resin beads from being carried from the tank by the withdrawn water.

Figure 3:
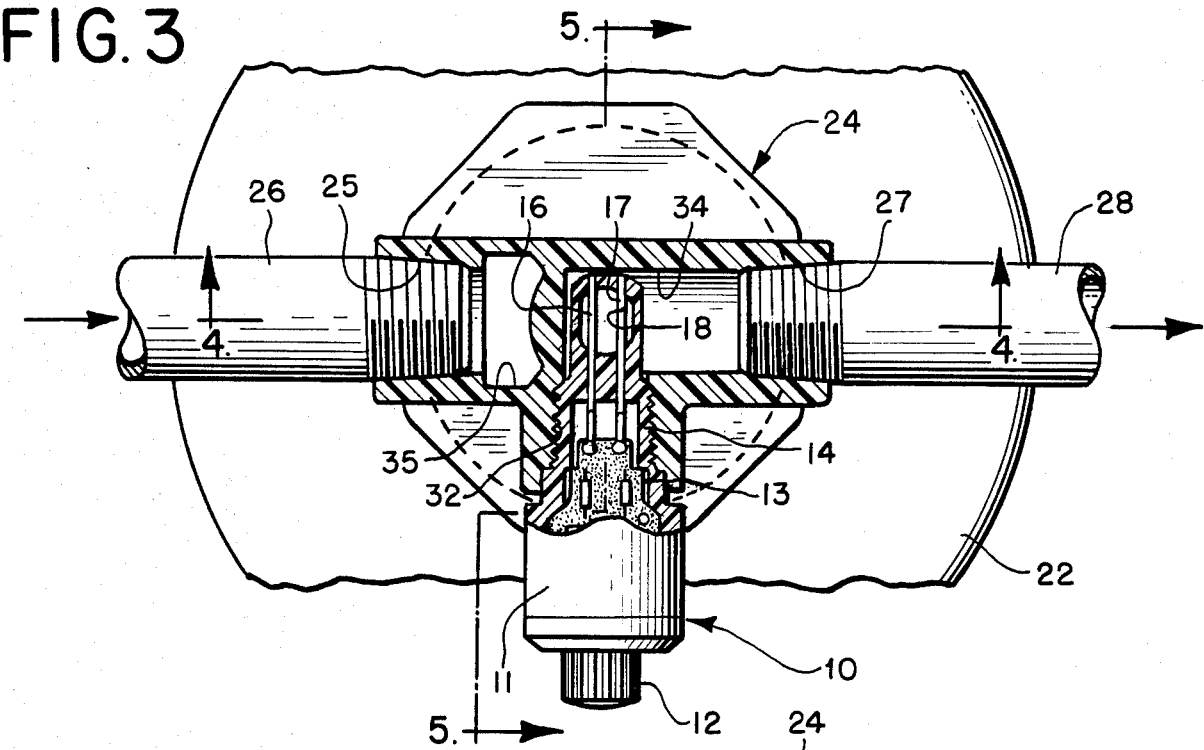
FIG. 3 is an enlarged cross-sectional view taken along line 3—3 of FIG. 2 showing the monitoring device installed on the adapter head of the deionization chamber.
Figure 4:
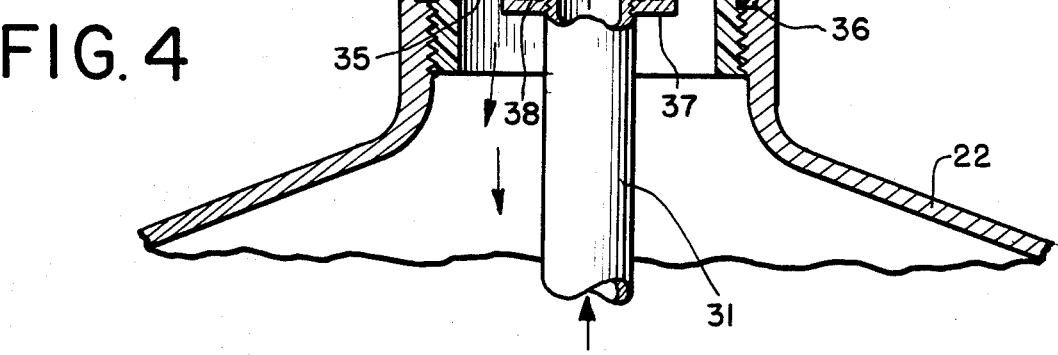
FIG. 4 is a cross-sectional view of the monitoring device and adapter head taken along line 4—4 of FIG. 3.
Figure 5:
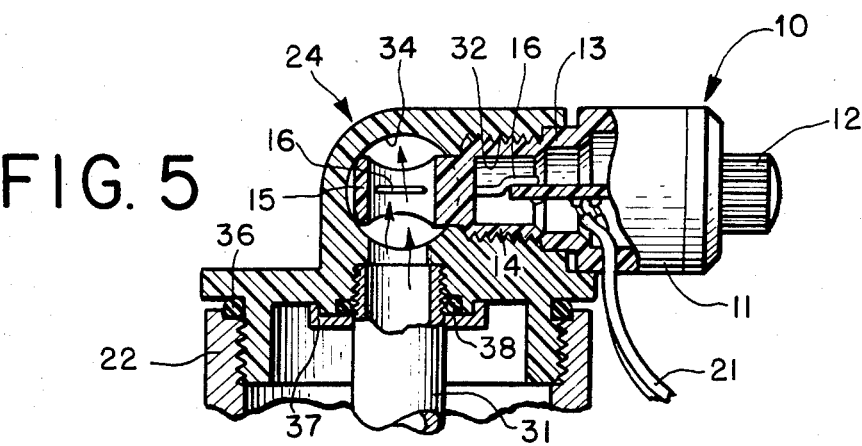
FIG. 5 is a cross-sectional view of the monitoring device and adapter head taken along line 5—5 of FIG. 3.

The adapter assembly 24 includes in accordance with conventional practice an internally threaded receptacle 32 within which the liquid conductivity monitor device 10 is received. As shown in FIGS. 3-5, when device 10 is received within receptacle 32 the conductivity sensing electrodes 16 and 17 of the device are interposed in an outlet passageway 34 within the head assembly so as to be continuously exposed to deionized water as it leaves the processing apparatus. Input water is discharged into tank 22 about the neck of the tank through a passageway 35 within the head assembly. The entire head assembly is in accordance with conventional practice threaded on the neck of processing tank 22 and sealed by conventional means such as an O-ring 36 (FIGS. 4 and 5).

The outlet conduit 31 of tank 22 may be attached to the body of adapter fitting 24 by means of a threaded connection, as shown in FIGS. 4 and 5. A threaded collar 37 and an O-ring 38 may be provided at the connection point for increased mechanical rigidity and to provide a better liquid seal between the outlet passageway 34 and the inlet passageway 35.

Figure 6:
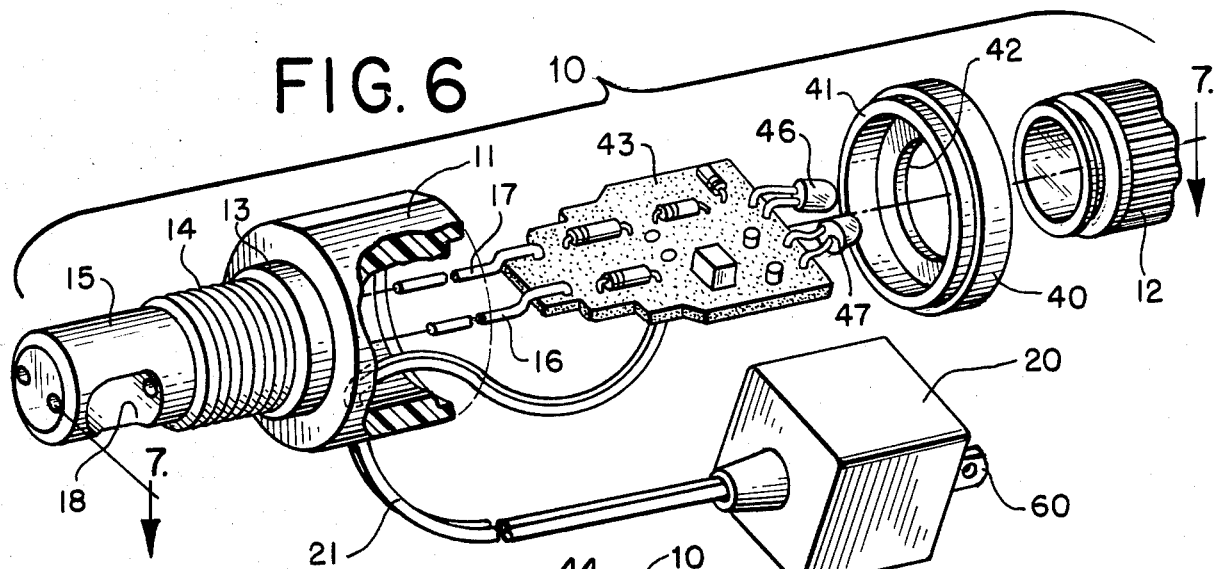
FIG. 6 is an exploded perspective view partially broken away of the principal components of the liquid conductivity monitoring device, of FIG. 1.
Figure 7:
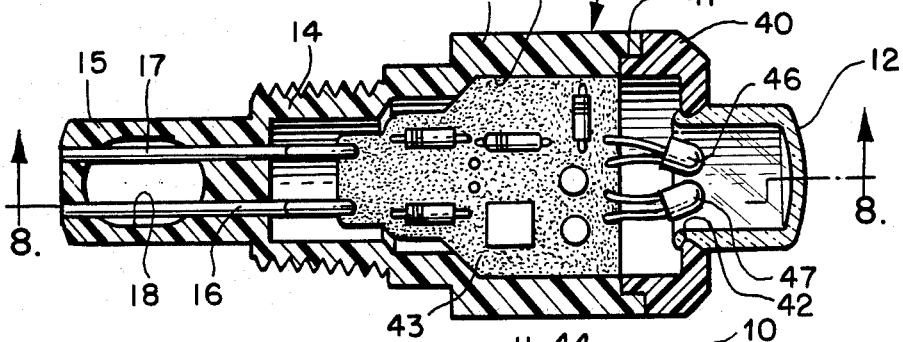
FIG. 7 is a cross-sectional view of the liquid conductivity monitoring device in an assembled state taken along line 7—7 of FIG. 6.
Figure 8:
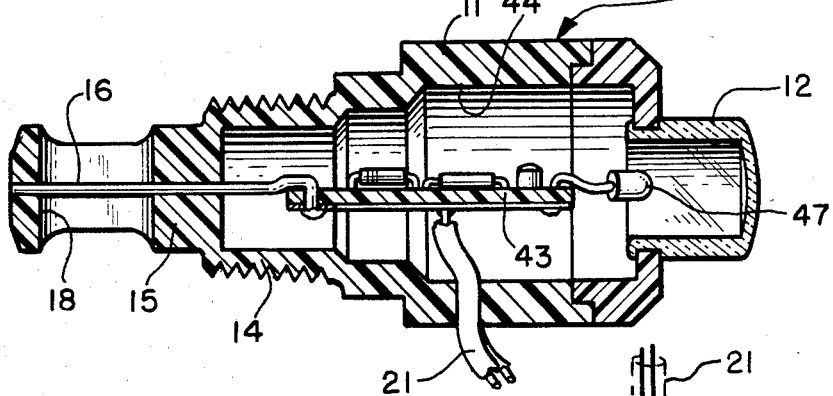
FIG. 8 is a cross-sectional view of the liquid conductivity monitoring device taken along line 8—8 of FIG. 7.

Referring to FIG. 6, the cylindrical body of monitor device 10 is seen to include an annular end cap 40 having a rim portion 41 for concentric engagement with the corresponding end of housing 11, and an aperture 42 for receiving the interior end of lens portion 12. When the central body portion 11, annular end cap 40 and lens portion 12 are assembled, as shown in FIGS. 7 and 8, an elongated liquidsealed housing of generally cylindrical proportions is formed.

To provide a support surface for the circuitry and circuit components of the monitoring device, a circuit board 43 is preferably provided within the interior 44 of the housing. As shown in FIGS. 7 and 8, circuit board 43 is preferably arranged in a plane parallel with the plane defined by sensing electrodes 16 and 17, and may be held in position within housing 11 by means of slots on either side of the interior wall of the housing. Sensing electrodes 16 and 17 extend in an axial direction through the probe, shank and body portions 15, 14 and 13 of the monitor device, and into contact with appropriately spaced connection pads on circuit board 43. To provide a visible indication of water status, the monitor device includes a red light emitting diode (LED) 46 and a green LED 47. Both LED's project into the transparent lens cap 12 so as to be visible to a user. The LED's are connected to circuit board 43 by conventional means such as connecting pads (not shown) integral to the printed circuitry of the circuit board.

Figure 9:
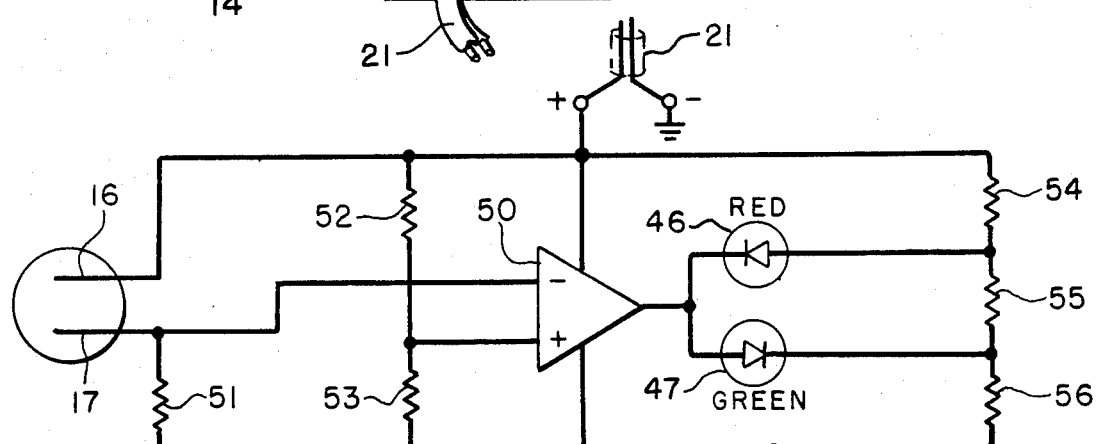
FIG. 9 is an electrical schematic diagram of the liquid conductivity monitoring device.

Referring to the electrical schematic diagram of FIG. 9, LED's 46 and 47 are controlled by a single operational amplifier 50 mounted to circuit board 43 within housing 11. This operational amplifier is connected in a conventional manner to operate as a comparator amplifier, and includes inverting and non-inverting inputs and a single output terminal. Operating power is supplied to the amplifier by connection to power pack 20, which may comprise a line-powered low-voltage unidirectional supply current source of conventional construction.

The inverting input of amplifier 50 is connected directed to sensing electrode 17, and through a resistor 51 to ground. The non-inverting input of the amplifier is connected through a resistor 52 to the supply current source, and through a resistor 53 to ground. The remaining sensing electrode 16 is connected directly to the supply current source.

The output terminal of amplifier 50 is connected to the cathode of LED 46 and to the anode of LED 47. Operating power for LED's 46 and 47 is derived from a pair of unidirectional current sources in the form of a voltage divider network comprising resistors 54-56. The anode of LED 46 is connected to the juncture of resistors 54 and 55. The cathode of LED 47 is connected to the juncture of resistors 55 and 56. Resistors 54-56 are connected across the supply current source such that a positive polarity signal or voltage (with reference to ground) at a first predetermined level is supplied to the anode of LED 46, and a second positive polarity signal or voltage at a second predetermined level is applied to LED 47.

When the conductivity between sensing electrodes 16 and 17 is low, as in the presence of pure or non-ionized water, the inverting input of the comparator has a higher voltage level than the non-inverting input, rendering the output of comparator amplifier 50 to a logic high, or to a relatively positive voltage level with respect to ground. Conversely, should the conductivity between sensing electrodes 16 and 17 increase, as in the presence of unpure or ionized water, the inverting input becomes positive relative to the reference non-inverting input, thereby reducing the voltage level at the output of comparator amplifier 50 to a logic low, or to a relatively low or zero voltage level with respect to ground.

In accordance with the invention, the predetermined signal or voltage levels developed by the voltage divider network comprising resistors 54, 55 and 56 for application to the cathode of LED 47 and the anode of LED 46 are each selected at an intermediate level between the logic high and logic low output signal levels of amplifier 50. As a result, the green LED 47 will be forward biased and light when the amplifier output is logic high, and the red LED 46 will be forward biased and light when the amplifier output is logic low. Thus, one or the other of the LED's is forward biased and lit at all times that the monitoring device is powered.

Resistors 54, 55 and 56 are selected such that current through LED's 46 and 47 is sufficient to provide a bright output indication but not so high as to reduce the life of the lamps. In practice, it has been found that a current flow through the LED's of approximately 0.025 ampere is desirably for optimum lamp life. Since the back-to-back configuration results in one of the LED's being forward biased at all times, the reverse bias which can be applied to the other non-conducting LED is automatically limited to safe levels.

In practice, for a selected power source 20 resistor 54 is selected to limit current flow through LED 46 when amplifier 50 is in a logic low (unpure) state, and resistor 56 is selected to limit current flow through LED 47 when amplifier 50 is in a logic high (pure) state. With resistors 54 and 56 thus selected, resistor 55 is selected such that the non-lit LED will always be back-biased. Thus, when the amplifier is logic high and LED 47 is lit, the signal or voltage level at the juncture of resistors 54 and 55, as applied to LED 46, is less than the logic high signal or voltage level at the amplifier, and LED 46 is back-biased and does not light. Conversely, when the amplifier is low and LED 46 is lit, the signal or voltage level at the juncture of resistors 55 and 56, as applied to LED 47, is greater than the logic low signal or voltage level at the amplifier, and LED 47 is back-biased and does not light.

If desired, one or both of the LED devices can be made to flash by substitution of a flashing LED component in a manner well known to the art. This is particularly desirable in connection with the red LED 46 to better call attention to an unsatisfactory purity condition.

Power supply 20 may comprise a conventional low voltage DC supply of the modular type having a pair of blade contacts 60 (FIG. 6) for direct insertion in a standard AC outlet. Conventional transformer and rectifier circuitry within the power supply modular housing rectifies the AC line voltage to produce a low voltage unidirectional source current, typically in the order of 9 volts DC, for operation of the liquid conductivity monitor device. The source current is supplied to the monitoring device through cable 21.

Since LED's 46 and 47 are situated in close proximity behind the clear lens cap 12, the operator is presented with a single condition-indicative indication through the lens. The two LED's may be slightly angled towards each other and the axis of housing 11, as shown in FIG. 7, to improve this display.

In the presence of pure or non-ionized water, wherein the conductivity between sensing electrodes 16 and 17 is low, only the green LED 47 lights and the operator is presented with a green output indication through the lens. In the event of unpure or ionized water being present, only LED 46 lights and the operator is presented with a red light in lens 12. Thus, during operation of the monitor device either the red LED 46 or the green LED 47 will be lit. In the event that neither LED is lit, the monitor device is either not powered, as when the power supply module 20 is unplugged, or the monitor device is defective and no output current is available at the output of comparator amplifier 50 for lighting the LED's. Thus, a continuous and unambiguous indication of water conductivity level is presented to the operator.

In one successful embodiment of the invention for use with a 9 VDC modular power supply, the circuit of the invention was constructed utilizing the following components:

Amplifier 50—Type LM 741C
Resistor 51—3.3 megaohms
Resistor 52—2700 ohms
Resistor 53—10,000 ohms
Resistor 55—330 ohms
Resistor 56—220 ohms
LED 46—Type SBR 5512
LED 47—Type ESBG 5521

It will be appreciated that the circuit of the invention can be constructed using other components, as required by a particular monitoring situation and supply current source. For example, in applications requiring increased sensitivity resistor 51 may be increased in value and the reference voltage applied to the non-inverting input of amplifier 50 be changed by selection of resistors 52 and 53.

The monitoring device of the invention can be installed in-line in any liquid conduit by use of an appropriate fitting, having an aperture for receiving the monitoring device. One form of such fitting is shown in FIGS. 10 and 11, wherein two conduit segments 60 and 61 are shown joined by a T-type fitting 62. A threaded aperture 63 on the side of the fitting receives the monitoring device, which has body, shank and probe portions 13, 14 and 15 dimensioned to position electrodes 16 and 17 in the lumen of the conduit. It will be appreciated that the length and diameter of the monitoring device may be increased or decreased as appropriate to accommodate various sizes of conduits.

Where independent current adjustment through LED's 46 and 47 is not required, it is possible to eliminate resistor 55, as shown in FIG. 12. With this circuit arrangement current flow through the LED's is dependent on the two voltage divider resistors 54 and 56. However, these resistors must together provide sufficient series resistance to limit the current drain through the voltage divider on the source supply to an acceptable level. The provision of resistor 55 in the circuit of FIG. 9 enables this current drain to be limited independently of resistors 54 and 56, which may then be optimized for desired current flow through LED's 46 and 47.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A monitoring device for monitoring electrical conductivity in a liquid, comprising, in combination:

a pair of spaced-apart conductivity-sensing electrodes arranged for immersion in the liquid;

comparison amplifier means having first and second input terminals and an output terminal, said first input terminal being coupled to said sensing electrodes, said second input terminal being coupled to a reference voltage source, the signal level developed by said comparison amplifier at said output terminal changing from first predetermined logic signal level of a predetermined polarity to a second predetermined logic signal level of the same polarity upon the conduction between said electrodes exceeding a predetermined threshold level dependent on said reference voltage source;

supply current means including a supply current source and a voltage divider comprising first, second and third resistance elements serially connected between said supply current source and ground, the juncture of said first and second resistance elements comprising a first unidirectional reference current source, and the juncture of said second and third resistance elements comprising a second unidirectional reference current source; and means including first and second light-emitting diodes independently and directly connected between respective ones of said first and second unidirectional reference current sources and said output terminal, said diodes being oppositely poled relative to said output terminal whereby said first light-emitting diode is forward biased to light when said output terminal is at said first predetermined logic signal level, and to not light when said output terminal is at said second predetermined logic level, to indicate liquid conductivity below said predetermined threshold level, and said second light-emitting diode is forward biased to light when said output terminal is at said second predetermined logic signal level, and to not light when said output terminal is at said first predetermined logic level, to indicate liquid conductivity above said predetermined threshold level.

2. A conductivity monitoring device as defined in claim 1 wherein the light outputs of said light-emitting diodes are of different colors.

3. A monitoring device for monitoring electrical conductivity in a liquid within a conduit flow system including an aperture in the wall thereof, said monitoring device comprising, in combination:

an elongated housing dimensioned at one end to fit through the aperture in the conduit;

a pair of spaced-apart conductivity-sensing electrodes arranged at the one end of the housing for immersion in the liquid when the one end of the housing is fitted through the aperture;

comparison amplifier means within the housing having first and second input terminals and an output terminal, said first input terminal being coupled to said sensing electrodes, said second input terminal being coupled to a reference voltage source, the signal level developed by said comparison amplifier on said output terminal changing from a first predetermined logic signal level of a predetermined polarity to a second predetermined logic signal level of the same polarity upon the conduction between said electrodes exceeding a predetermined threshold level dependent on said reference voltage source;

supply current means including a supply current source and a voltage divider comprising first, second and third resistance elements serially connected between said supply current source and ground, the juncture of said first and second resistance elements comprising a first unidirectional current source, and the juncture of said second and third resistance elements comprising a second unidirectional current source; and means including first and second light-emitting diodes arranged at the opposite end of said housing and viewable from the exterior thereof, said diodes being independently and directly connected between respective ones of said first and second unidirectional current sources and said output terminal, and being oppositely poled relative to said output terminal whereby said first light-emitting diode is forward biased to light when said output terminal is at said first predetermined logic level, and to not light when said output terminal is at said second predetermined logic level, to indicate conductivity in the liquid is below said predetermined threshold level, and said second light-emitting diode is forward biased to light when said output terminal is at said second predetermined logic signal level, and to not light when said output terminal is at said first predetermined logic signal level, to indicate conductivity in the liquid is above said predetermined threshold level.

4. A conductivity monitoring device as defined in claim 3 wherein the light outputs of said light-emitting diodes are of different colors.

5. A conductivity monitoring device as defined in claim 4 wherein said housing includes a lens portion at said other end for rendering said light-emitting diodes viewable from the exterior of the housing.

6. A conductivity monitoring device as defined in claim 3 wherein said housing is generally cylindrical in form and is threaded at said one end for insertion into the aperture in the conduit.

7. A monitoring device for monitoring electrical conductivity in a liquid, comprising, in combination:

a pair of spaced-apart conductivity-sensing electrodes arranged for immersion in the liquid;

comparison amplifier means having first and second input terminals and an output terminal, said first input terminal being coupled to said sensing electrodes, said second intput terminal being coupled to a reference voltage source, the signal level developed by said comparison amplifier at said output terminal changing from a first predetermined logic signal level of a predetermined polarity to a second predetermined logic signal level of the same polarity upon the conduction between said electrodes exceeding a predetermined threshold level dependent on said reference voltage source;

supply current means including a supply current source and a voltage divider comprising at least first and second resistance elements serially connected between said supply current source and ground, the juncture of said first and second resistance elements comprising a reference current source; and means including first and second light-emitting diodes independently and directly connected between said reference current source and said output terminal, said diodes being oppositely poled relative to said output terminal whereby said first light-emitting diode is forward biased to light when said output terminal is at said first predetermined logic signal level, and to not light when said output terminal is at said second predetermined logic level, to indicate liquid conductivity below said predetermined threshold level, and said second light-emitting diode is forward biased to light when said output terminal is at said second predetermined logic signal level, and to not light when said output terminal is at said first predetermined logic level, to indicate liquid conductivity above said predetermined threshold level.

8. A conductivity monitoring device as defined in claim 7 wherein the light outputs of said light-emitting diodes are of different colors.

9. A monitoring device for monitoring electrical conductivity in a liquid within a conduit flow system including an aperture in the wall thereof, said monitoring device comprising, in combination:

an elongated housing dimensioned at one end to fit through the aperture in the conduit;

a pair of spaced-apart conductivity-sensing electrodes arranged at the one end of the housing for immersion in the liquid when the one end of the housing is fitted through the aperture;

comparison amplifier means within the housing having first and second input terminals and an output terminal, said first input terminal being coupled to said sensing electrodes, said second input terminal being coupled to a reference voltage source, the signal level developed by said comparison amplifier on said output terminal changing from a first predetermined logic signal level of a predetermined polarity to a second predetermined logic signal level of the same polarity upon the conduction between said electrodes exceeding a predetermined threshold level dependent on said reference voltage source;

supply current means including a supply current source and a voltage divider comprising at least first and second resistance elements serially connected between said supply current source and ground, the juncture of said first and second resistance elements comprising a reference current source; and means including first and second light-emitting diodes arranged at the opposite end of said housing and viewable from the exterior thereof, said diodes being independently and directly connected between said reference current source and said output terminal, and being oppositely poled relative to said output terminal whereby said first light-emitting diode is forward biased to light when said output terminal is at said first predetermined logic level, and to not light when said output terminal is at said second predetermined logic level, to indicate conductivity in the liquid is below said predetermined threshold level, and said second light-emitting diode is forward biased to light when said output terminal is at said second predetermined logic signal level, and to not light when said output terminal is at said first predetermined logic signal level, to indicate conductivity in the liquid is above said predetermined threshold level.

10. A conductivity monitoring device as defined in claim 9 wherein the light outputs of said light-emitting diodes are of different colors.

11. A conductivity monitoring device as defined in claim 10 wherein said housing includes a lens portion at said other end for rendering said light-emitting diodes viewable from the exterior of the housing.

12. A conductivity monitoring device as defined in claim 9 wherein said housing is generally cylindrical in form and is threaded at said one end for insertion into the aperture in the conduit.

* * * * *